United States Patent
Zimmermann

(10) Patent No.: US 7,942,963 B2
(45) Date of Patent: *May 17, 2011

(54) MAGNESIUM AMMONIUM PHOSPHATE CEMENT COMPOSITION

(75) Inventor: Michael Zimmermann, Frankfurt (DE)

(73) Assignee: Kyhon SARL, Neuhatel (CH)

(*) Notice: Subject to any disclaimer, the term of this patent is extended or adjusted under 35 U.S.C. 154(b) by 0 days.

This patent is subject to a terminal disclaimer.

(21) Appl. No.: 12/727,643

(22) Filed: Mar. 19, 2010

(65) Prior Publication Data

US 2010/0173846 A1 Jul. 8, 2010

Related U.S. Application Data

(63) Continuation of application No. 12/463,880, filed on May 11, 2009, which is a continuation of application No. 11/841,651, filed on Aug. 20, 2007, now Pat. No. 7,540,914, which is a continuation of application No. 11/530,835, filed on Sep. 11, 2006, now Pat. No. 7,431,763, which is a continuation of application No. 11/104,392, filed on Apr. 11, 2005, now Pat. No. 7,115,163, which is a continuation of application No. 10/772,857, filed on Feb. 4, 2004, now Pat. No. 6,908,506, which is a continuation of application No. 10/070,670, filed as application No. PCT/EP01/07605 on Jul. 3, 2001, now Pat. No. 6,692,563.

(30) Foreign Application Priority Data

Jul. 3, 2000 (DE) .................................. 100 32 220

(51) Int. Cl.
C04B 12/02 (2006.01)
(52) U.S. Cl. ..................................................... 106/690
(58) Field of Classification Search .................. 106/690
See application file for complete search history.

(56) References Cited

U.S. PATENT DOCUMENTS

| | | |
|---|---|---|
| 3,746,680 A | 7/1973 | Boricheski |
| 4,141,864 A | 2/1979 | Rijke et al. |
| 4,192,021 A | 3/1980 | Deibig et al. |
| 4,239,113 A | 12/1980 | Gross et al. |
| 4,341,691 A | 7/1982 | Anuta |
| 4,404,327 A | 9/1983 | Crugola et al. |
| 4,518,430 A | 5/1985 | Brown et al. |
| 4,588,583 A | 5/1986 | Pietsch et al. |
| 4,612,053 A | 9/1986 | Brown et al. |
| 4,629,464 A | 12/1986 | Takata et al. |
| 4,678,436 A | 7/1987 | Kondo et al. |
| 4,721,659 A | 1/1988 | Tieckelmann et al. |
| 4,722,948 A | 2/1988 | Sanderson |
| 4,791,150 A | 12/1988 | Braden et al. |
| 4,872,936 A | 10/1989 | Engelbrecht |
| 4,902,649 A | 2/1990 | Kimura et al. |
| 4,940,689 A | 7/1990 | Ito |
| 4,957,352 A | 9/1990 | Yasuda et al. |
| 4,959,104 A | 9/1990 | Iino et al. |
| 5,004,501 A | 4/1991 | Faccioli et al. |
| 5,108,956 A | 4/1992 | Inoue et al. |
| 5,149,368 A | 9/1992 | Liu et al. |
| 5,160,371 A | 11/1992 | Ito |
| 5,171,720 A | 12/1992 | Kawakami |
| 5,179,065 A | 1/1993 | Ito |
| 5,204,382 A | 4/1993 | Wallace et al. |
| 5,205,928 A | 4/1993 | Inoue et al. |
| 5,226,877 A | 7/1993 | Epstein |
| 5,262,166 A | 11/1993 | Liu et al. |
| 5,276,070 A | 1/1994 | Arroyo |
| 5,281,265 A | 1/1994 | Liu |
| 5,352,715 A | 10/1994 | Wallace et al. |
| 5,462,722 A | 10/1995 | Liu et al. |
| 5,522,893 A | 6/1996 | Chow et al. |
| 5,545,254 A | 8/1996 | Chow et al. |
| 5,605,713 A | 2/1997 | Boltong |
| 5,650,108 A | 7/1997 | Nies et al. |
| 5,695,729 A | 12/1997 | Chow et al. |
| 5,795,922 A | 8/1998 | Demian et al. |
| 5,797,873 A | 8/1998 | Franz et al. |
| 5,814,683 A | 9/1998 | Branham |
| 5,847,046 A | 12/1998 | Jiang et al. |
| 5,952,010 A | 9/1999 | Constantz |
| 6,002,065 A | 12/1999 | Constantz et al. |
| 6,075,067 A | 6/2000 | Lidgren |
| 6,124,373 A | 9/2000 | Peter et al. |
| 6,153,664 A | 11/2000 | Wise et al. |
| 6,187,046 B1 | 2/2001 | Yamamoto et al. |
| 6,203,574 B1 | 3/2001 | Kawamura |
| 6,206,957 B1 | 3/2001 | Driessens et al. |
| 6,224,635 B1 | 5/2001 | Ricci et al. |
| 6,231,615 B1 | 5/2001 | Preissman |
| 6,241,734 B1 | 6/2001 | Scribner et al. |
| 6,248,110 B1 | 6/2001 | Reiley et al. |
| 6,273,916 B1 | 8/2001 | Murphy |
| 6,309,420 B1 | 10/2001 | Preissman |
| 6,325,992 B1 | 12/2001 | Chow et al. |
| 6,338,810 B1 | 1/2002 | Carpena et al. |
| 6,436,143 B1 | 8/2002 | Ross et al. |
| 6,521,264 B1 | 2/2003 | Lacout et al. |
| 6,547,866 B1 | 4/2003 | Edwards et al. |
| 6,562,755 B1 | 5/2003 | Halbrook, Jr. et al. |

(Continued)

FOREIGN PATENT DOCUMENTS

DE 29607832 10/1996

(Continued)

OTHER PUBLICATIONS

Abdullah et al., Biodegradable Polymeric Bone Cement Formed from Hydroxyapatite, Poly (Propylene Fumerate), Poly (Vinyl Pyrrolidone) and Benzoyl Peroxide, Materials Science and Technology, vol. 20, No. 9, pp. 1084-86 (2004) (abstract only).

(Continued)

Primary Examiner — Paul Marcantoni

(57) ABSTRACT

This invention relates to a cement, which comprises in its main phase of microcrystalline magnesium ammonium phosphate and nanoapatite after hardening and thus at the same time has considerable strength. The material is biologically degradable and is suitable for application in tooth cements, as bone replacement, as bone filler, as bone cement or as bone adhesive.

13 Claims, No Drawings

U.S. PATENT DOCUMENTS

| | | | |
|---|---|---|---|
| 6,593,394 B1 | 7/2003 | Li et al. | |
| 6,613,054 B2 | 9/2003 | Scribner et al. | |
| 6,692,563 B2 * | 2/2004 | Zimmermann | 106/696 |
| 6,908,506 B2 * | 6/2005 | Zimmermann | 106/696 |
| 6,953,594 B2 | 10/2005 | Lee et al. | |
| 6,994,726 B2 | 2/2006 | Lin et al. | |
| 7,008,433 B2 | 3/2006 | Voellmicke et al. | |
| 7,115,163 B2 * | 10/2006 | Zimmermann | 106/35 |
| 7,135,027 B2 | 11/2006 | Delmotte | |
| 7,138,442 B2 | 11/2006 | Smith et al. | |
| 7,160,932 B2 | 1/2007 | Schilke et al. | |
| 7,273,523 B2 | 9/2007 | Wenz | |
| 7,431,763 B2 * | 10/2008 | Zimmermann | 106/690 |
| 7,540,914 B2 | 6/2009 | Zimmermann | |
| 2001/0012968 A1 | 8/2001 | Preissman | |
| 2002/0152929 A1 | 10/2002 | Burgath et al. | |
| 2002/0167480 A1 | 11/2002 | Johnson et al. | |
| 2002/0187104 A1 | 12/2002 | Li et al. | |
| 2002/0191487 A1 | 12/2002 | Sand | |
| 2003/0031698 A1 | 2/2003 | Roeder et al. | |
| 2003/0032964 A1 | 2/2003 | Watkins et al. | |
| 2003/0055512 A1 | 3/2003 | Genin et al. | |
| 2003/0139488 A1 | 7/2003 | Wojciak | |
| 2003/0161858 A1 | 8/2003 | Lidgren | |
| 2003/0180344 A1 | 9/2003 | Wise et al. | |
| 2004/0048947 A1 | 3/2004 | Lidgren et al. | |
| 2004/0122359 A1 | 6/2004 | Wenz et al. | |
| 2004/0157952 A1 | 8/2004 | Soffiati et al. | |
| 2004/0173122 A1 | 9/2004 | Zimmermann | |
| 2004/0226479 A1 | 11/2004 | Lyles et al. | |
| 2004/0265385 A1 | 12/2004 | West | |
| 2005/0105384 A1 | 5/2005 | Eder et al. | |
| 2005/0199156 A1 | 9/2005 | Khairoun et al. | |
| 2005/0246036 A1 | 11/2005 | Zimmermann | |
| 2005/0256220 A1 | 11/2005 | Lavergne et al. | |
| 2006/0079905 A1 | 4/2006 | Beyar et al. | |
| 2007/0021526 A1 | 1/2007 | He et al. | |
| 2007/0022912 A1 | 2/2007 | Zimmermann | |
| 2007/0032567 A1 | 2/2007 | Beyar et al. | |
| 2007/0048382 A1 | 3/2007 | Meyer et al. | |
| 2007/0128245 A1 | 6/2007 | Rosenberg et al. | |
| 2007/0191964 A1 | 8/2007 | Preissman | |
| 2007/0254011 A1 | 11/2007 | Schnabelrauch et al. | |

FOREIGN PATENT DOCUMENTS

| | | |
|---|---|---|
| DE | 20218668 | 3/2003 |
| DE | 20218668 U1 | 3/2003 |
| EP | 0473048 A2 | 3/1992 |
| EP | 0511868 A2 | 11/1992 |
| EP | 0520690 A2 | 12/1992 |
| EP | 0543765 A1 | 5/1993 |
| EP | 1002513 A1 | 5/2000 |
| EP | 0835668 B1 | 11/2007 |
| JP | 01320251 | 12/1989 |
| JP | 02116684 | 5/1990 |
| WO | WO9202478 A1 | 2/1992 |
| WO | WO9513835 A1 | 5/1995 |
| WO | WO9614265 A1 | 5/1996 |
| WO | WO0149327 A2 | 7/2001 |
| WO | WO0232827 A1 | 4/2002 |
| WO | WO03086327 A2 | 10/2003 |
| WO | WO03103734 A1 | 12/2003 |
| WO | WO2004050131 A1 | 6/2004 |
| WO | WO2005009481 A2 | 2/2005 |
| WO | WO2007025633 A2 | 3/2007 |
| WO | WO2007067561 A2 | 6/2007 |
| WO | 2007145824 A3 | 12/2007 |

OTHER PUBLICATIONS

Baroud et al., Influence of Oscillatory Mixing on the Injectability of Three Acrylic and Two Calcium-Phosphate Bone Cements for Vertebroplasty, J Biomed Mater Res, vol. 68B, No. 1, pp. 105-11 (2004) (abstract only).

Beruto et al., Use of Alpha-Tricalcium Phosphate (TCP) as Powders and as an Aqueous Dispersion to Modify Processing, Microstructure, and Mechanical Properties of Polymethylmethacrylate (PMMA) Bone Cements and to Produce Bone-Substitute Compounds, J Biomed Mater Res, vol. 49, No. 4, pp. 498-505 (2000) (abstract only).

Bezzi G. et al., A novel sol-gel technique for hydroxyapatite preparation, Materials Chemistry and Physics, 2003, 78: 816-824, entire document.

Bonfield et al., Hydroxyapatite Composite Biomaterials—Evolution and Applications, Materials World, vol. 5, No. 1, pp. 18-20 (1997).

Brown, et al., A new calcium phosphate, water-setting cement, Cements Research Progress 1986 pp. 352-379 (1987).

Canul-Chuil et al., Comparative Study of Bone Cements prepared with either HA or alpha-TCP and Functionalized Methacrylates, J Biomed Mater Res, vol. 64B. No. 1, pp. 27-37 (2003) (abstract only).

Chu et al., Hydroxyapatite/PMMA Composites as Bone Cements, Biomed Mater Eng, vol. 14, No. 1, pp. 87-105 (2004) (abstract only).

Dalby et al., Initial Interaction of Osteoblasts with the Surface of a Hydroxyapatite-Poly (Methylmethacrylate) Cement, Biomaterials, vol. 22, No. 13, pp. 1739-1747 (2001) (abstract only).

Eule et al., Bioactive Bone Cement: The Solution for Osteolysis and Late Implant Loosening, SRS Annual Meeting: Scientific Program Abstracts, pp. 98 (2002).

Frankenburg et al., Evaluation of Hydroxyapatite/Bis-GMA Bone Cement for Fixation of Cemented Hip Stems, The Third Combined Meeting of the Orthopaedic Research Societies of the USA, Canada, Europe and Japan, Hamamatsu City, Japan (1998).

Grigorian et al., Evolution of Tissue Structures in the Mandible after Implantation of Plate from Polymethylmethacrylate and its Compositions with Hydroxyapatite, Stomatolgiia, vol. 82, No. 2, pp. 10-14 (2003) (abstract only).

Harper et al., Tensile Characteristics of Ten Commerical Acrylic Bone Cements, J Biomed Mater Res:Appl Biomater., vol. 53, pp. 605-616 (2000) (abstract only).

Heness et al., Biocomposite—Bone Cement, Hydroxyapatite and Biomimetic Composites for Bone Repair, Innovative Bioceramics, Materials Forum, vol. 27 (2004) (3 page abstract).

Hitchon et al., Comparison of the Biomechanics of Hydroxyapatite and Polymethylmethacrylate Vertebroplasty in a Cadaveric Spinal Compression Fracture Model, J. Neurosurg, vol. 95, Suppl. 2, pp. 215-220, (2001) (abstract only).

Jager et al., Comprehensive Biocompatibility Testing of a New PMMA-hA Bone Cement Versus Conventional PMMA Cement in Vitro, J. Biomater Sci Polym Ed, vol. 14, No. 11, pp. 1283-1298 (2003) (abstract only).

Lee C L et al., Laser Ablation of Dyed Acrylic Bone Cement, Lasers in Surgery and Medicine, Wiley-Liss, New York, US vol. 20, 3, Jan. 1, 1997, pp. 280-289, XP000694435, ISSN:0196-8092.

Lee R.R. et al, Interactions between bone and hydroxyapatite filled 4 META/MMA-TBB adhesive cement in vitro and in physiological environment, 1996, IEEE Xplore, pp. 18-21, entire document.

Li et al., A Novel Injectable Bioactive Bone Cement for Spinal Surgery: A Developmental and Preclinical Study, J Biomed Mater Res, vol. 52, No. 1,,pp. 164-170 (2000) (abstract only).

Liu et al., Influence of the Aspect Ratio of Bioactive Nanofillers on Rheological Behavior of PMMA-Based Orthopedic Materials, J Biomed Mater Res, vol. 71B, No. 1, pp. 116-122 (2004) (abstract only).

Liao et al., A Fundamental Study on Bioreactions of Sr-HA, Hua Xi Kou Qiang Yi Xue Za Zhi, vol. 20, No. 3, pp. 172-174 183 (2002) (abstract only).

Miyazaki et al., Bioactive PMMA Bone Cement Prepared by Modification with Methacryloxypropyltrimethoxysilane and Calcium Chloride, J Biomed Mater Res, vol. 67A, No. 4, pp. 1417-1423 (2003) (abstract only).

Mousa et al., Biological and Mechanical Properties of PMMA-Based Bioactive Bone Cements, Biomaterials, vol. 21, No. 21, pp. 2137-2146 (2000) (abstract only).

Okada et al., Transmission Electron Microscopic Study of Interface Between Bioactive Bone Cement and Bone: Comparison of Apatite and Wollastonite Containing Glass-Ceramic Filler with Hydroxyapatite and Beta-Tricalcium Phosphate Filler, J Biomed Mater Res, vol. 45, No. 4, pp. 277-284 (1999) (abstract only).

Oonishi et al., Hydroxyapatite Granules Interposed at Bone-Cement Interface in Total Hip Replacements: Histological Study of Retrieved Specimens, J Biomed Mater Res, vol. 53, No. 2, pp. 174-180 (2000) (abstract only).

Patel et al., Comparison of Sintering and Mechanical Properties of Hydroxyapatite and Silicon-Substituted Hydroxyapatite, Key Engineering Materials, 240-242, 919-22 (2003) (abstract only).

Patent Abstract XP-002180738 (1 page total), Park et al., "Compositional effects of CaO-SiO2-P2O5 bioactive cement on hardening and hydroxyapatite formation" Yoop Hakhoechi, 31(5):502-512 (1994).

Patent Abstract XP-002180739 (1 page total), Nippon Electric Glass Co., "Bone-repair material for fast, strong bonding—contains glass and/or crystalline glass powder, a.q. phosphate solution and bond formation promoter" (1992).

The term "PRE-", Merriam-Webster Online Dictionary, at the web: http://www.m-w.com, p. 1-2.

Serbetci et al., Mechanical and Thermal Properties of Hydroxyapatite-Impregnated Bone Cement, Turk J Med Sci, vol. 30, pp. 543-549 (2000) (abstract only).

Turner et al., Hydroxyapatite Composite Resin Cement Augmentation of Pedicle Screw Fixation, Clinical Orthopaedics & Related Research, vol. 1, No. 406, pp. 253-261 (2003) (abstract only).

Wong et al., In Vivo Cancellous Bone Remodeling on a Strontium-Containing Hydroxyapatite (sr-HA) Bioactive Cement, J Biomed Mater Res A, vol. 68, No. 3, pp. 513-521 (2004) (abstract only),).

Wong et al., Ultrastructural Study of Mineralization of a Strontium-Containing Hydroxyapatite (Sr-HA) Cement in Vivo, J Biomed Mater Res A, vol. 70, No. 3, pp. 428-435 (2004) (abstract only.

Zhao et al., Surface Treatment of Injectable Strontium-Containing Bioactive Bone Cement for Vertebroplasty, J. Biomed Mater Res B Appl Biomater, vol. 69, No. 1, pp. 79-86 (2004) (abstract only).

International Search Report, WIPO, Jan. 22, 2009.

International Search Report and Written Opinion, International Application No. PCT/US2007/012723, mailed Dec. 3, 2008.

International Search Report and Written Opinion, International Application No. PCT/US2007/008789, mailed Nov. 13, 2008.

International Search Report and Written Opinion, International Application No. PCT/EP2006/007750, mailed Jun. 11, 2007.

International Search Report, International Application No. PCT/US03/38580, mailed May 19, 2004.

International Search Report, International Application No. PCT/US2005/014616, mailed Sep. 12, 2005.

Heini, P.F., et al., "Bone substitutes in vertebroplasty," *Eur. Spine J.*, Jun. 14, 2001, vol. 10, pp. S205-S213.

Li, Y., et al. "Preparation of amorphous calcium phosphate in the presence of poly(ethylene glycol)," *Journal of Materials Science Letters*, 2003, vol. 22, pp. 1015-1016.

\* cited by examiner

MAGNESIUM AMMONIUM PHOSPHATE CEMENT COMPOSITION

CROSS-REFERENCES TO RELATED APPLICATIONS

This application is a continuation of Ser. No. 12/463,880, filed May 11, 2009, which is a continuation of application Ser. No. 11/841,651, filed Aug. 20, 2007, now U.S. Pat. No. 7,540,914, which is a continuation of application Ser. No. 11/530,835, filed Sep. 11, 2006, now U.S. Pat. No. 7,431,763, which is a continuation of application Ser. No. 11/104,392, filed Apr. 11, 2005, now U.S. Pat. No. 7,115,163, which is a continuation of application Ser. No. 10/772,857, filed Feb. 4, 2004, now U.S. Pat. No. 6,908,506, which is a continuation of application Ser. No. 10/070,670, filed Mar. 4, 2002, now U.S. Pat. No. 6,692,563, which was a §371 National Phase of PCT/EP01/07605, filed on Jul. 3, 2001, which claimed priority from DE 100 32 220, filed on Jul. 3, 2000, the full disclosures of which are incorporated herein by reference.

BACKGROUND OF THE INVENTION

Field of the Invention

The invention relates to a magnesium ammonium phosphate cement preparation, a process for its production and an associated use.

This invention relates in particular to a biologically degradable cement, which consists in its main phase of magnesium ammonium phosphates and nanoapatites after hardening and thus at the same time has a high strength.

The material may be used as bone replacement, for bone augmentation and for bone regeneration.

It may serve as excipient for pharmaceutical or biological active ingredients.

The most important mineral constituents in human bone and tooth enamel are calcium and phosphate. However, considerable quantities of sodium, magnesium and carbonate are also present.

It is known from precipitation studies of synthetic systems that sodium ions and carbonate ions may be incorporated very easily into calcium phosphate precipitates resulting in a molecular structure similar to apatite.

However, magnesium has a strong tendency to precipitate in a different structure not similar to apatite.

Calcium phosphate precipitated physiologically as bone and dentine is nanocrystalline. It cannot be seen from an X-ray diffractogram, due to line broadening, whether it is apatite or other structures.

Some scientists are of the opinion that so much magnesium occurs in bone and dentine that this cannot all be taken up in the apatite structure. Therefore, a mixed form of the mineral of nanoapatite and nanodolomite or nanostruvite is assumed here.

Calcium phosphates are not only biocompatible but are recognized by the living cell as belonging-to-the-body. Therefore, there are many biomaterials and medical products which consist partly of calcium phosphate.

Calcium phosphate ceramics have been on the market since about 1970, partly in the form of prefabricated blocks or as granules.

Implantations of these materials in bone structures are predominantly successful.

The biggest disadvantage of these systems is that the blocks have to be prefabricated and the granules drift away (flood out) from the side of the implantation. This often leads to failure of such implantations.

Calcium phosphate ceramics are most successful when they consist of hydroxyl-apatite (HA) or of beta-tertiary calcium phosphate (β-TCP, a whitlockite-like structure) or when the calcium phosphate ceramics consist of both, HA and β-TCP in variable ratios. HA is virtually non-resorbable from bone implantations, whereas β-TCP is slowly resorbed and replaced by new bone.

It is therefore possible to influence the degree of resorption of calcium phosphate ceramic by changing the β-TCP/HA ratio.

It is likewise possible to admix other resorbable materials, such as: monetite $CaHPO_4$, brushite $CaHPO_4\text{-}2H_2O$, calcite $CaCO_3$ and dolomite $CaMg(CO_3)_2$.

Since 1985 attempts have been made to develop calcium phosphate cements in order to avoid the disadvantages of prefabricated or granular-like calcium phosphate ceramics (W. E. Brown and L. C. Chow, "A new calcium phosphate, water-setting cement", Cem. Res. Prog. 1986 352-379 (1987)).

This includes a brushite cement not yet commercially available having a Ca/P molar ratio of the precipitated phase of 1.00. This phase is not nanocrystalline but microcrystalline.

All the other calcium phosphate cements developed hitherto have a nanocrystalline precipitation structure and a Ca/P molar ratio of $>=1.5$, which may be further increased by addition of carbonate. These materials are known under U.S. Pat. No. 5,605,713; European application 0 835 668; World 96/14265, and some of these materials are already on the market.

There are contradictory reports regarding the resorbability of these materials after implantations in bone and soft tissue.

In each case, calcium phosphate cements based on hydroxylapatite (HA) which are not resorbable (HA ceramics see above) and calcium phosphate cements based on deficient calcium hydroxylapatites (CDHA, calcium deficient hydroxylapatites) which are good osteotransductively, are differentiated.

This means for the last-mentioned case, that they may be resorbed by osteoclasts and may be replaced by new bone tissue from osteoblasts.

Resorption of these cements depends crucially on the local bone transformation mechanisms.

Today, most surgeons require a calcium phosphate cement, in which initially a mechanically supporting mode of action is brought to bear, but the final resorption lags behind independently of the local transformation mechanisms of the bone, that is that the material is completely degraded. In addition, it is known in orthopaedics that vital bone only remains where it is required from the biomechanical point of view. This is known as the so-called Wolff's Law. Consequently, if a calcium phosphate cement introduced into a bone defect has a higher compressive strength than the bone surrounding it and this high compressive strength remains unchanged, this leads to degradation of bone tissue lying around the implant (here calcium phosphate cement).

In order to fulfill this requirement, even if only partly, some manufacturers have admixed substances into their CDHA cements which are similar to nanoapatite, which are passively resorbed by the bodily fluids due to the concentration gradients, such as for example monetite ($CaHPO_4$) or calcite ($CaCO_3$) as known from European 0 543 765.

However, this only partly solves the problem. A cement is also required which can be resorbed completely passively and in which the resorption front and the deposition front are in direct contact.

Gypsum for example does not fulfill this requirement. Gypsum is resorbed so rapidly that there is always a gaping hole between the resorption front and the deposition front and these materials do not have adequate supporting function due to their low resistance to pressure. Such materials are disclosed, for example under U.S. Pat. No. 5,281,265.

For these reasons, it is desirable to provide a bone replacement material, which initially takes over the lost supporting function of the bone with high resistance to pressure, but then successively decreases in resistance to pressure, as a result of which the endogenous bone transformation processes (remodeling) are stimulated and hence more rapid osteoneogenesis and hence also active resorption of the bone replacement material is introduced. This may also be achieved by incorporating a slightly soluble substance, for example into a hardening cement paste. Because bone grows well into macroporous structures, it is advantageous to admix granular or pellet-like, solubilizing substances consisting of, for example sugars, salts (for example NaCl) or gypsum ($CaSO_4$) into the cement paste. They are then leached out very rapidly in the body from the hardened cement structure and a porous sponge-like structure remains. Production of a porous (finished) cement outside the body is also conceivable.

In order to be able to use a cement for dental applications, such as for example filling and scaling of small dentine channels, filling of tooth cavities after vital extirpation, utilizing such a cement as sub-filling material in endodontology, such a material may not shrink to prevent passage of bacteria. Even a material having low-grade expandable properties would be desirable.

It is the object of the invention to provide a cement preparation, with which the disadvantages of the state of the art are avoided.

BRIEF SUMMARY OF THE INVENTION

The present invention provides a magnesium ammonium phosphate cement preparation, comprising: a powder mixture having molar quantities of the components calcium (Ca), magnesium (Mg) and orthophosphate (P) in the mixture in the ranges $1.00<Ca/P<1.50$ and $0<Mg/P<0.50$; an ammonium salt; and water and/or an aqueous solution.

In one embodiment, the present invention provides a magnesium ammonium phosphate cement preparation, comprising: a powder mixture, consisting of ($\alpha$-TCP, $\beta$-TCP, $MgHPO_4 \times 3H_2O$, $KH_2PO_4$ and $Na_2HPO_4$; an ammonium salt; and water and/or an aqueous solution.

In another embodiment, the present invention provides a magnesium ammonium phosphate cement preparation, comprising: a powder mixture consisting of: $\alpha/\beta$-TCP, $MgHPO_4 \times 3H_2O$, $KH_2PO_4Na_2HPO_4$ and $Mg_3(PO_4)_2$; and an aqueous solution containing ammonium ions.

In a further embodiment, the present invention provides a magnesium ammonium phosphate cement preparation, comprising: a powder mixture consisting of: $\alpha/\beta$-TCP, $MgHPO_4 \times 3H_2O$, $KH_2PO_4Na_2HPO_4$ and $Mg_3(PO_4)_2$; and an aqueous solution containing ammonium ions.

In yet another embodiment, the present invention provides a magnesium ammonium phosphate cement preparation, comprising: a powder mixture consisting of: $\alpha/\beta$-TCP, $MgHPO_4 \times 3H_2O$, $KH_2PO_4Na_2HPO_4$ and $Mg_3(PO_4)_2$; and an aqueous solution containing ammonium ions.

The preparations of the present invention can also include one or more of the following features:
  the aqueous solution is an aqueous solution of an ammonium salt having a pH value in the range from $7<pH<12$;
  the ammonium salt is present in the powder mixture and the molar quantities of the components calcium (Ca), magnesium (Mg), orthophosphate (P) and ammonium ($NH_4$) lie in the ranges $1.00<Ca/P<1.50$ and $0<Mg/P<0.50$ and $0<NH_4<0.50$;
  the powder mixture comprises $\alpha/\beta$-tertiary calcium phosphate ($\alpha/\beta$-TCP) and preferably $MgHPO_4 \times 3H_2O$;
  the powder mixture, apart from $\alpha/\beta$-TCP and $MgHPO_4 \times 3H_2O$, additionally contains $Mg_3(PO_4)_2$;
  the aqueous solution comprises an aqueous $(NH_4)_2SO_4$ solution;
  the powder mixture comprises $(NH_4)_2SO_4$;
  a mixing liquid consists of an aqueous $(NH_4)_2HPO_4$ solution;
  the powder mixture additionally comprises $KH_2PO_4$;
  the powder mixture additionally comprises $Na_2HPO_4$;
  additionally $SrCO_3$;
  the level of $SrCO_3$ is 0.01 to 10 wt. %, preferably 0.1 to 5 wt. %, based on the total weight of the preparation;
  an aqueous solution of an ammonium salt as mixing liquid;
  an aqueous solution of a magnesium salt as mixing liquid;
  as additional component, ZnO in the powder mixture and/or in the mixing liquid;
  the powder mixture additionally contains $Ca_2NaK(PO_4)_2$ and/or $CaKPO_4$;
  as an additional component, fluoride ions in the powder mixture and/or in the mixing liquid; and
  as additional components, pharmaceutical and/or bioactive active ingredients in the powder mixture and/or in the mixing liquid, preferably antibiotics, cytostatic agents, analgesics, disinfectants, growth factors, proteins or elastin inhibitors in therapeutic doses.

The invention also provides a process for producing a magnesium ammonium phosphate cement wherein the powder mixture is mixed with the mixing liquid while achieving uniform distribution of the liquid in the powder mixture and the paste thus obtained is applied on or to the target zone or is introduced into the target zone and is allowed to harden, wherein the components react such that the cement formed has microcrystalline magnesium ammonium phosphate.

In another embodiment, the invention provides a process for producing a magnesium ammonium phosphate cement using a magnesium ammonium cement preparation, in which the powder mixture is mixed with the mixing liquid while achieving uniform distribution of the liquid in the powder mixture and the paste thus obtained is applied on or to the target zone or is introduced into the target zone and is allowed to harden with formation of cement containing microcrystalline magnesium ammonium phosphate.

The process in accord with the present invention also can include one or more of the following features:
  granular, thus granular particles which are slightly soluble in aqueous liquids, between about 10 μm and about 300 μm, preferably between 50 μm and 200 μm, are added to the powder mixture; and
  the granular particles preferably consist of NaCl, sugars, $CaSO_4$, $\beta$-TCP, polylactides, polyglycolides or polylactide/polyglycolide copolymer, $CaCO_3CaHPO_4$.

The preparations of the present invention can be used, e.g., for medical purposes, for tooth cement and for bone replacement or bone filler or bone cement or bone adhesive.

DETAILED DESCRIPTION OF THE INVENTION

The problems in the state of the art are preferably solved by the present invention to the effect that it is possible to set the ability for expansion of the hardening cement paste by variation in the admixture of strontium salts. In tests, as shown in the examples, it is namely shown that the ability for expansion of the cement mixture, the main phase of which is the magnesium ammonium phosphate in the hardened state, decreases with increasing weight portion of strontium salts in the total powder mixture. Consequently, with this invention a material for endodontology may be provided, which also has an expandable property in addition to adequate mechanically loadable stability.

An object of this invention is to provide a material for bone replacement, for bone augmentation and bone regeneration, which may be resorbed in a limited time and the resistance to pressure of which may decrease adapted to the regeneration requirements of the body.

Another object of the invention to provide a material that may be created, prepared and modeled under normal temperature conditions, preferably body temperature, in other words a cement.

It is characteristic of the material provided, that it may additionally be adjusted by the intensity of the degree of sintering of the $Mg_3(PO_4)_2$ introduced in its processing time, in particular at room temperature, wherein the rate of solubility on the surface of these particles is controlled by the degree of sintering and the density of the $Mg_3(PO_4)_2$ used resulting therefrom, so that the precipitation of the Ca/Mg/phosphate compound settling out necessary for solidification may be controlled.

Furthermore, it is the object of this invention to provide a phosphate cement having partial solubility, preferably due to the slow solubility of the magnesium ammonium phosphate apatite structure (cement).

Furthermore, it is the object of the present invention to describe a reaction process, which leads to the formation of a magnesium ammonium phosphate cement from a number of individual components and which hardens in a clinically acceptable time at room and/or body temperature.

Furthermore, it is the object of the present invention to provide a material which becomes adequately hard and stable in a clinically acceptable time and which has a strong ability for adhesion to mineralized surfaces.

Furthermore, the object of the invention is the material disclosed according to the invention which is characterized by a strong ability for adhesion to metallic surfaces.

Furthermore, it is the object of the present invention to provide a resorbable cement, which can be injected in the form of a mixed paste.

One aspect of this invention is that the end product consists of a powder mixture having a molar Ca/P ratio in the range from 1.00 to 1.50. (P represents orthophosphate).

In addition, it is essential that the molar ratio Mg/P ratio of this powder mixture includes the range from 0 to 1.00.

In order to mix and to shape a cement paste, which hardens within an acceptable time, these powder mixtures must be adequately reactive. In order to achieve this, a further aspect of this invention is to mix the powder mixtures with suitable quantities of slightly basic (7<pH<12), aqueous solutions of soluble ionic constituents, such as for example: $Na_3PO_4$, $K_2CO_3$ and/or $Na_2CO_3$ in combination with $(NH_4)_2HPO_4$.

A further feature of this invention is that granular but granular solids which are thus slightly soluble in the bodily fluid are admixed to the hardening cement paste, so that after settling-out thereof, a microporous to macroporous pore system results.

A further aspect of this invention is that these cements reach their maximum solidity within a few hours.

A further feature of this invention lies in the ability for expansion of the cement during setting. The expansivity is determined or adjusted by the relative proportion of an admixed strontium salt.

A further feature of this invention is that the hardened cement consists of microcrystalline magnesium ammonium phosphate.

A further feature of this invention is that the initial hardening time of the cement may be set at 1 to 40 minutes and the final hardening time at 2.5 to 60 minutes. (according to ASTM C266-89)

A further feature of this invention is that the cement may reach a maximum compressive strength of over 50 MPa.

A further feature of this invention is that the cement paste can be injected before reaching the initial hardening time.

A further feature of this invention is that the cement paste may serve as excipient for other materials which are not Ca, Mg and/or phosphate. For example ZnO, pharmaceutical active ingredients (antibiotics, cytostatic agents, growth factors) or other bioactive substances.

Further features and advantages of the invention can be seen from the description of exemplary embodiments.

EXAMPLES

The following symbols are used in the examples:
P=powder mixture
L=liquid
L/P=liquid/powder ratio in ml/g
$t_i$=initial hardening time (according to ASTM standard C266-89, Gilmoore needle)
$t_F$=final (end) hardening time (according to ASTM standard C266-89, Gilmoore needle)
D(x h)=compressive strength in Mpa after x hours storage in 0.9% strength NaCl solution at 37° C.

Production: After weighing out all constituents, the powder mixture is homogenized in a ball mill for about 20 minutes.

Example 1

| | | | |
|---|---|---|---|
| P = | 60 g α-$Ca_3(PO_4)_2$ + | | |
| | 6 g $MgHPO_4 \cdot 3H_2O$ + | | |
| | 5 g $MgSO_4 \cdot 7H_2O$ | | |
| L = | 2M $(NH_4)_2HPO_4$ | L/P = | 0.40 |
| $t_i$ = | 9 | $T_F$ = | 21 |
| D (18) | 18.4 ± 1.5 | | |
| D (72) | 26.1 ± 4.0 | | |

Example 2

| | | | |
|---|---|---|---|
| P = | 60 g α-$Ca_3(PO_4)_2$ + | | |
| | 14 g $MgHPO_4 \cdot 3H_2O$ + | | |
| | 2 g $Mg(OH)_2$ | | |
| L = | 3.5 M $(NH_4)_2HPO_4$ | L/P = | 0.35 |
| $t_i$ = | 3 | $T_F$ = | 7 |
| D(18) | 32.5 ± 3.5 | | |
| D(72) | 46.9 ± 5.4 | | |

Example 3

| | | | |
|---|---|---|---|
| P = | | 60 g α-Ca$_3$(PO$_4$)$_2$ + | |
| | | 16 g MgHPO$_4$•3H$_2$O + | |
| | | 3 g Na(PO$_4$)$_3$•12H$_2$O | |
| L = | 3.5 M (NH$_4$)$_2$HPO$_4$ | L/P = | 0.35 |
| $t_i$ = | 6 | $T_F$ = | 14 |
| D(18) | 44.7 ± 3.4 | | |
| D(72) | 51.7 ± 5.0 | | |

Example 4

| | | | |
|---|---|---|---|
| P = | | 60 g α-Ca$_3$(PO$_4$)$_2$ + | |
| | | 14 g MgHPO$_4$•3H$_2$O + | |
| | | 2 g ZnO | |
| L = | 3.5 M (NH$_4$)$_2$HPO$_4$ | L/P = | 0.35 |
| $t_i$ = | 6 | $T_F$ = | 23 |
| D(18) | 35.1 ± 5.3 | | |
| D(72) | 42.9 ± 0.8 | | |

Example 5

| | | | |
|---|---|---|---|
| P = | | 45 g CaHPO$_4$•2H$_2$O + | |
| | | 14 g MgHPO$_4$•3H$_2$O + | |
| | | 6 g Mg(OH)$_2$ | |
| L = | 2 M (NH$_4$)$_2$HPO$_4$ | L/P = | 0.40 |
| $t_i$ = | 2.5 | $T_F$ = | 7.5 |
| D(18) | 3.8 ± 1.2 | | |

Example 6

| | | | |
|---|---|---|---|
| P = | | 45 g CaHPO$_4$•2H$_2$O + | |
| | | 14 g CaCO$_3$ + | |
| | | 14 g MgHPO$_4$•3H$_2$O + 6 g ZnO | |
| L = | 3.5 M (NH$_4$)$_2$HPO$_4$ | L/P = | 0.35 |
| $t_i$ = | 2 | $T_F$ = | 4 |
| D(18) | 3.8 ± 1.2 | | |

Example 7

| | | | |
|---|---|---|---|
| P = | | 60 g α-Ca$_3$(PO$_4$)$_2$ + | |
| | | 16 g MgHPO$_4$•3H$_2$O + | |
| | | 5 g β-Ca$_3$(PO$_4$)$_2$ | |
| L = | 3.5 M (NH$_4$)$_2$HPO$_4$ | L/P = | 0.35 |
| $t_i$ = | 4 | $T_F$ = | 9 |
| D(2) | 59.3 ± 1.0 | | |
| D(4) | 55.6 ± 5.0 | | |
| D(18) | 61.6 ± 5.0 | | |
| D(72) | 51.5 ± 6.6 | | |
| D(18d) | 28.1 ± 4.6 | | |

Example 8

| | | | |
|---|---|---|---|
| P = | | 60 g α-Ca$_3$(PO$_4$)$_2$ + | |
| | | 16 g MgHPO$_4$•3H$_2$O + | |
| | | 5 g β-Ca$_3$(PO$_4$)$_2$ | |
| L = | 3.5 M (NH$_4$)$_2$HPO$_4$ | L/P = | 0.35 |
| $t_i$ = | 3.5 | $T_F$ = | 11.5 |
| D(2) | 54.4 ± 3.3 | | |
| D(18) | 65.6 ± 5.3 | | |
| D(4d) | 56.6 ± 8.6 | | |
| D(18d) | 36.3 ± 2.4 | | |
| D(30d) | 30.0 ± 3.0 | | |

Example 9

| | | | |
|---|---|---|---|
| P = | | 60 g α-Ca$_3$(PO$_4$)$_2$ + | |
| | | 16 g MgHPO$_4$•3H$_2$O + | |
| | | 5 g β-Ca$_3$(PO$_4$)$_2$ + 0.8 g SrCO$_3$ | |
| L = | 3.5 M (NH$_4$)$_2$HPO$_4$ | L/P = | 0.35 |
| $t_i$ = | 5.5 | $T_F$ = | 13 |
| D(2.5) | 54.3 ± 4.6 | | |
| D(5) | 61.1 ± 5.5 | | |
| D(18) | 70.1 ± 5.7 | | |
| D(4d) | 74.3 ± 9.3 | | |
| D(18d) | 43.4 ± 3.4 | | |
| D(30d) | 34.0 ± 4.0 | | |

Example 10

| | | | |
|---|---|---|---|
| P = | | 60 g α-Ca$_3$(PO$_4$)$_2$ + | |
| | | 8 g MgHPO$_4$•3H$_2$O + | |
| | | 2 g (NH$_4$)$_2$SO$_4$ + | |
| | | 2 g KH$_2$PO$_4$ + 3.5 g SrCO$_3$ | |
| L = | 3.5 M (NH$_4$)$_2$HPO$_4$ | L/P = | 0.30 |
| $t_i$ = | | $T_F$ = | |
| D(0.25) | 11.2 ± 0.8 | | |
| D(0.5) | 17.2 ± 1.8 | | |
| D(2) | 31.7 ± 1.3 | | |
| D(6) | 39.7 ± 0.63 | | |
| D(3d) | 56.5 ± 4.9 | | |

Example 11

| | | | |
|---|---|---|---|
| P = | | 60 g α-Ca$_3$(PO$_4$)$_2$ + | |
| | | 8 g MgHPO$_4$•3H$_2$O + | |
| | | 4 g (NH$_4$)H$_2$PO$_4$ + 1 g SrCO$_3$ | |
| L = | 3.5 M (NH$_4$)$_2$HPO$_4$ | L/P = | 0.37 |
| $t_i$ = | | $T_F$ = | |
| D(2) | 22.6 ± 1.0 | | |
| D(6) | 31.4 ± 1.1 | | |
| D(18) | 45.8 ± 1.8 | | |
| D(3d) | 45.7 ± 2.9 | | |
| D(35d) | 11.5 ± 1.2 | | |

Example 12

| | |
|---|---|
| P = | 60 g α-Ca$_3$(PO$_4$)$_2$ + 17.4 g MgHPO$_4$•3H$_2$O + 7 g (NH$_4$)$_2$SO$_4$ + 1.7 g SrCO$_3$ |
| L = | 3.5 M (NH$_4$)$_2$HPO$_4$    L/P = 0.35 |
| t$_i$ = | T$_F$ = |
| D(2) | 43.3 ± 2.9 |
| D(6) | 45.4 ± 4.4 |
| D(18) | 45.8 ± 1.8 |
| D(3d) | 45.7 ± 2.9 |
| D(28d) | 19.5 ± 5.1 |

Example 13

| | |
|---|---|
| P = | 60 g α-Ca$_3$(PO$_4$)$_2$ + 20 g CaHPO$_4$ + 8 g CaCO$_3$ + 1 g MgHPO$_4$ + 1.7 g SrCO$_3$ |
| L = | 3.5 M (NH$_4$)$_2$HPO$_4$    L/P = 0.35 |
| t$_i$ = | 2.5    T$_F$ = 8 |
| D(2) | 43.3 ± 2.9 |
| D(6) | 49.4 ± 3.7 |
| D(18) | 54.3 ± 2.5 |
| D(3d) | 53.6 ± 3.1 |
| D(28d) | 54.5 ± 1.9 |

Example 14

| | |
|---|---|
| P = | 60 g β-Ca$_3$(PO$_4$)$_2$ + 17.4 g MgHPO$_4$•3H$_2$O + 1.7 g SrCO$_3$ |
| L = | 3.5 M (NH$_4$)$_2$HPO$_4$    L/P = 0.35 |
| t$_i$ = | 3.5    T$_F$ = 9 |

Example 15

| | |
|---|---|
| P = | 60 g α-TCP + 34.8 g MgHPO$_4$ x 3H$_2$O + 13.2 g (NH$_4$)SO$_4$ |
| L = | 5% NaHCO$_3$    L/P = 0.35 |
| t$_i$ = | 3    T$_F$ = 10 |

Example 16

| | |
|---|---|
| P = | 60 g α-TCP + 16 g MgHPO$_4$ x 3H$_2$O + 5 g β-TCP + 20 g NaCL (diameter 150 μm) |
| L = | 3.5 M (NH$_4$)$_2$HPO$_4$    L/P = 0.35 |
| t$_i$ = | 5    T$_F$ = 12 |

Example 17

P=60 g α-TCP+6 g Mg$_3$(PO$_4$)$_2$+10 g KH$_2$PO$_4$+5 β-TCP
Mixing solution: 3.2 molar solution (NH$_4$)$_2$HPO$_4$
L/P=0.35
T$_i$=10.8 t$_f$=20
D(2)–18.5±1.0
D(18)=48.3±1.8

While the above is a complete description of the preferred embodiments of the invention, various alternatives, modifications, and equivalents may be used. Therefore, the above description should not be taken as limiting the scope of the invention which is defined by the appended claims.

What is claimed is:

1. A magnesium ammonium phosphate cement produced by a process comprising: providing an ammonium salt; providing a powder mixture having molar quantities of the components calcium (Ca), magnesium (Mg) and orthophosphate (P) in the mixture in the ranges 1.00<Ca/P<1.50 and 0<Mg/P<0.50; mixing the ammonium salt and the powder mixture with a mixing liquid to form a paste and achieve an uniform distribution of the liquid in the powder mixture; and reacting the components therein to form a microcrystalline magnesium ammonium phosphate cement.

2. The magnesium ammonium phosphate cement of claim 1, further comprising providing a strontium salt.

3. The magnesium ammonium phosphate cement of claim 2, wherein the strontium salt comprises SrCO$_3$.

4. The magnesium ammonium phosphate cement of claim 3, comprising providing the SrCO$_3$ in a quantity of 0.01 to 10 wt. % based on the total weight of the preparation.

5. The magnesium ammonium phosphate cement of claim 1, comprising providing the ammonium salt as (NH$_4$)$_2$HPO$_4$.

6. The magnesium ammonium phosphate cement of claim 1, comprising reacting the components therein between about 2.5 to about 60 minutes (measured according to ASTM C266-89) to form the magnesium ammonium phosphate cement.

7. The magnesium ammonium phosphate cement of claim 1, further comprising providing granular particles.

8. The magnesium ammonium phosphate cement of claim 7, wherein the granular particles are slightly soluble in aqueous liquids.

9. The preparation of claim 7, comprising providing granular particles having a diameter of between 10 μm and 300 μm.

10. The magnesium ammonium phosphate cement of claim 7, wherein the granular particles are a substance selected from the group consisting of NaCl, sugars, CaSO$_4$, β-TCP, polylactides, polyglycolides or polylactide/polyglycolide copolymer, CaCO$_3$ and CaHPO$_4$.

11. The magnesium ammonium phosphate cement of claim 1, further comprising adding a pharmaceutical and/or a bioactive active ingredient.

12. The magnesium ammonium phosphate cement of claim 11, wherein the pharmaceutical and/or a bioactive active ingredient comprises a component selected from the group consisting of antibiotics, cytostatic agents, analgesics, disinfectants, growth factors, proteins and elastin inhibitors.

13. The magnesium ammonium phosphate cement of claim 1, comprising providing a powder mixture having α-tricalcium phosphate.

* * * * *